United States Patent [19]

Radisch, Jr. et al.

[11] Patent Number: 5,209,727
[45] Date of Patent: May 11, 1993

[54] GUIDE WIRE WITH INTEGRAL ANGIOPLASTY BALLOON

[75] Inventors: Herbert R. Radisch, Jr., San Diego; Andrew F. Farr, Spring Valley, both of Calif.

[73] Assignee: Interventional Technologies, Inc., San Diego, Calif.

[21] Appl. No.: 827,330

[22] Filed: Jan. 29, 1992

[51] Int. Cl.⁵ .................................. A61M 29/00
[52] U.S. Cl. ..................................... 604/96; 606/194
[58] Field of Search .................. 606/191–195; 604/95–103; 128/772, 657

[56] References Cited

U.S. PATENT DOCUMENTS

| | | |
|---|---|---|
| 4,140,126 | 2/1979 | Choudhury . |
| 4,141,364 | 2/1979 | Schultze . |
| 4,292,974 | 10/1981 | Fogarty et al. . |
| 4,406,656 | 9/1983 | Hattler et al. . |
| 4,608,984 | 9/1986 | Fogarty . |
| 4,627,436 | 12/1986 | Leckrone . |
| 4,685,458 | 8/1987 | Leckrone . |
| 4,686,982 | 8/1987 | Nash . |
| 4,705,517 | 11/1987 | DiPisa, Jr. . |
| 4,787,388 | 11/1988 | Hofmann . |
| 4,813,934 | 3/1989 | Engelson et al. .............. 604/99 |
| 4,838,268 | 6/1989 | Keith et al. ................... 606/194 |
| 4,875,481 | 10/1989 | Higgins ......................... 606/194 |
| 4,896,669 | 1/1990 | Bhate et al. . |
| 4,917,088 | 4/1990 | Crittenden .................... 606/194 |
| 4,946,466 | 8/1990 | Pinchuk et al. ............... 606/194 |
| 5,002,559 | 3/1991 | Tower ............................. 604/96 |
| 5,042,985 | 8/1991 | Elliott et al. . |
| 5,102,390 | 4/1992 | Crittenden et al. ........... 606/194 |

*Primary Examiner*—C. Fred Rosenbaum
*Assistant Examiner*—William Lewis
*Attorney, Agent, or Firm*—Nydegger & Associates

[57] ABSTRACT

An angioplasty device for dilating the lumen of a human blood vessel has a balloon and a tubular guide wire bonded to one end of the balloon. The guide wire is in fluid communication with the balloon. A guide extension is bonded to the opposite end of the balloon from the guide wire. An elongated spring member is positioned within the balloon, and is bonded at one end of the spring to the guide wire and at the opposite end of the spring to the guide extension to interconnect the wire and the extension. The spring member is attached between the wire and the extension in compression to urge the balloon into a collapsed configuration when the balloon is not inflated with fluid. The guide wire is strengthened by bonding a helical structural member to the outer wall of the guide wire.

24 Claims, 2 Drawing Sheets

GUIDE WIRE WITH INTEGRAL ANGIOPLASTY BALLOON

FIELD OF THE INVENTION

The present invention relates generally to devices for opening undesired stenoses in the vessels and fluid passageways of a living body. More specifically, the present invention relates to expandable balloon catheters which are positionable inside the lumen of a blood vessel and which may be expanded to open a stenotic segment in the lumen during an angioplasty procedure. The present invention is particularly, though not exclusively, useful in angioplasty applications which require relatively rapid inflation and deflation of a steerable balloon catheter.

BACKGROUND OF THE INVENTION

A wide variety of angioplasty devices exist for dilating the lumen of a body vessel, such as a vein or artery. Many of these angioplasty devices use expandable balloon catheters which are positioned inside the blood vessel at the point where the lumen is to be dilated, such as at an area of the lumen which has been constricted by arteriosclerotic plaque. In accordance with accepted procedures, once the catheter has been properly positioned within the blood vessel, the expandable balloon catheter is inflated with fluid. As the balloon expands, it dilates the lumen of the blood vessel to compress the obstructive tissue and open the constriction. After the constriction or stenosis has been opened, the balloon is deflated and removed to permit the restoration of blood flow in the vein or artery.

One means by which a balloon catheter may be positioned inside the blood vessel is to attach it to a guide wire, and then insert the combined catheter and guide wire into the vessel. In the case of other angioplasty balloon catheters, however, a guide tube or wire is prepositioned in the artery before the balloon catheter is inserted. Of course, one disadvantage with such a balloon catheter is that it requires two insertion procedures. On the other hand, when the guide wire is integrated with the balloon catheter, only one insertion procedure is required. Regardless which system is employed, a guide wire or some other stable platform with a low profile is required to properly position the relatively flexible and easily bent balloon.

To be effective, an integrated guide wire/balloon catheter must have certain characteristics. For instance, it must be functional for both positioning the catheter inside the body and for communicating fluid to and from the balloon. To do this, the guide wire should be hollow, yet have a small enough outside diameter to fit within and through a blood vessel. Further, and somewhat at odds with its requirement for a small outer diameter, the guide wire/balloon catheter should also have a large enough inside diameter for its lumen to permit adequate fluid communication through the catheter to the balloon. As can be readily appreciated, a relatively large lumen for the catheter is desirable to provide for relatively rapid inflation and deflation of the balloon. This capability is needed to minimize the time during which blood flow through the vessel is substantially impeded by an inflated balloon. Increasing the catheter's lumen while maintaining a necessarily small outer diameter, however, decreases its wall thickness and hence its structural strength. As can readily be appreciated, a structurally weak hollow guide wire may kink or deform, or may provide insufficient catheter steerablity and pushability during the insertion procedure. Stated differently, a guide wire should preferably be strong enough to withstand a relatively large amount of bending during the insertion process without buckling or undergoing plastic deformation. Further, the patency of the lumen is essential to allow for rapid deflation of the balloon and removal of the catheter if the patient should become distressed.

In addition to the above considerations, a balloon catheter mounted on the end of a positioning guide wire may become distorted and twisted when torque is applied to it as the guide wire is being inserted and steered into a curved blood vessel. Catheter twist is undesirable because it tends to collapse the lumen of the catheter and thus inhibit rapid and complete balloon expansion when fluid is infused into the balloon. Additionally, catheter twist is undesirable because it impedes effective transmission of torque from the guide wire's proximal end to the steerage distal end, which is effectively being steered.

In light of the above discussion, the present invention provides for a guide wire with integral angioplasty balloon which allows for relatively rapid inflation and deflation of the angioplasty balloon. Further, the present invention provides for a guide wire with integral angioplasty balloon which may be easily and effectively inserted into a human blood vessel in a single insertion procedure. Still further, the present invention provides for a guide wire with integral angioplasty balloon which is steerable into the lumen of a body vessel but which will not unduly distort or kink during insertion. The present invention provides for a guide wire with integral angioplasty balloon which may be easily and effectively positioned at a desired location within the blood vessel. Additionally, the present invention provides for a guide wire with integral angioplasty balloon which, together as a single unit, substantially prevents balloon through the catheter's guide wire. Finally, the present catheter windup when torque is applied to the catheter invention provides for a guide wire with integral angioplasty balloon which is relatively easy to manufacture and comparatively cost-effective.

SUMMARY OF THE INVENTION

An angioplasty device for dilating the lumen of a human blood vessel includes a polymeric balloon fixedly attached in axial alignment between a flexible hollow composite tube portion and a bendable guide extension. The hollow composite tube serves as a guide wire having one end connected to the hollow balloon portion and its other end connected to an angioplasty control device. The balloon is further attached around an elongated flexible spring-like structural member which is attached at one of its ends to the guide extension and at its other end to the tube portion and the guide wire. Thus, the flexible structural member interconnects the guide extension with the guide wire. When the balloon cross section is expanded by infusing the balloon with fluid through the hollow guide wire, the flexible structural member inside the balloon compresses to allow the balloon to expand. On the other hand, the flexible structural member inside the balloon elongates when the balloon is deflated, to collapse the balloon and stretch it into a cross section which is substantially equal to the cross section of the guide wire.

Additionally, a helical structural member is wound around the guide wire to strengthen the guide wire. Finally, a hydrophilic plug is positioned in the distal end of the balloon, i.e. the portion of the balloon that is connected to the guide extension. The hydrophilic plug allows the passage of air through the plug (until the plug has been substantially wetted) and out the guide extension to facilitate expelling air from the balloon as fluid is infused into the balloon through the hollow guide wire.

The novel features of this invention, as well as the invention itself, both as to its structure and its operation, will be best understood from the accompanying drawings, taken in conjunction with the accompanying description, in which similar reference characters refer to similar parts, and in which:

DESCRIPTION OF THE PREFERRED EMBODIMENT

Figure 1:
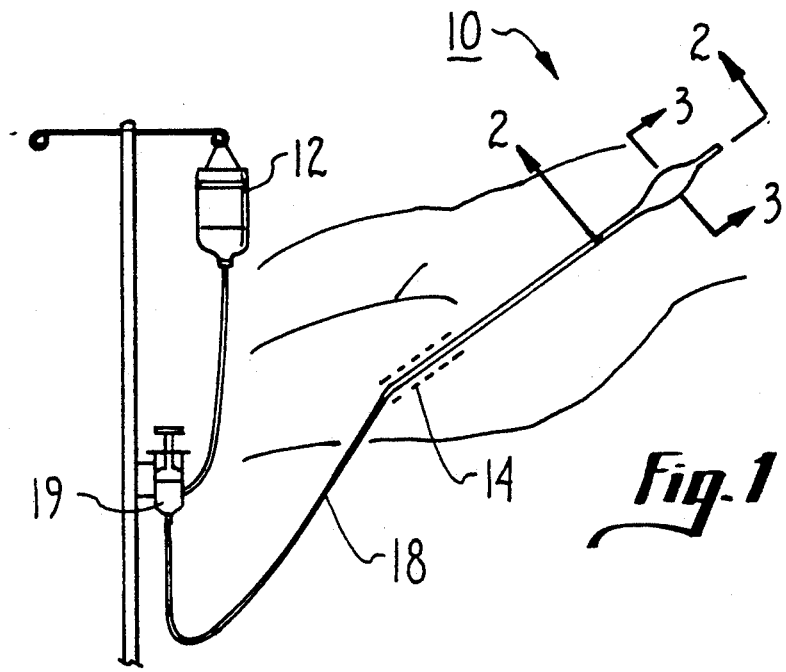
FIG. 1 is a perspective view of the angioplasty catheter device inserted into a human blood vessel.

Initially referring to FIG. 1, it can be seen that an angioplasty catheter device, generally designated 10, is attached to a fluid source 12 and inserted into a blood vessel 14 (shown in phantom) in preparation for an angioplasty procedure. Fluid source 12 provides fluid for expanding balloon 16 by infusion of fluid through hollow guide wire 18. As will be appreciated by the skilled artisan, any pumping device may be used which is suitable for pumping fluid from source 12 into guide wire 18. For example, a hand-held syringe pump 19 may be used for this purpose.

Figure 2:
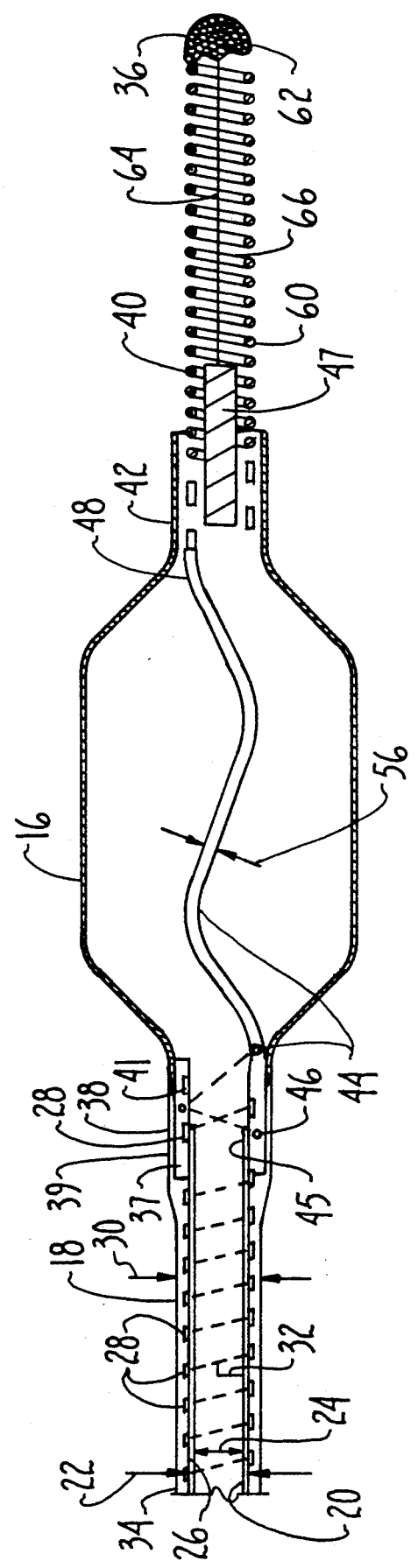
FIG. 2 is a cross-sectional view of the angioplasty catheter device with an inflated balloon as seen along the line 2—2 in FIG. 1.

The details of angioplasty catheter device 10 are best seen in reference to FIG. 2. There, it will be seen that hollow guide wire 18 includes a tube 20 through which fluid from source 12 may be pumped to and from balloon 16. As shown in FIG. 2, the balloon 16 is in its inflated state. It is to be appreciated that, when balloon 16 is deflated (as shown in FIG. 3B), the outer diameter 30 of tube 18 is small enough to permit insertion of angioplasty catheter device 10 into the blood vessel 14. At the same time, inner diameter 24 of tube 20 is large enough to facilitate relatively rapid expansion and deflation of balloon 16. In the present invention, inner diameter 24 is preferably about fourteen thousandths (0.014) of an inch thick and tube wall 26 is approximately one thousandth (0.001) of an inch thick, resulting in an outer diameter 22 for tube 20 of approximately sixteen thousandths (0.016) of an inch. Furthermore, tube wall 26 is composed of a high strength, yet flexible, material such as stainless steel. In addition, as is generally the case with all the materials of angioplasty catheter device 10, the material of tube wall 26 should be non-oxidizing and non-toxic, in order to be compatible with both the fluid from source 12 and with the body materials contacted by angioplasty catheter device 10.

Still referring to FIG. 2, a helical strengthening member 28 is shown bonded to tube wall 26. Although the present invention uses a wire for member 28, it is to be understood that the geometry of member 28 may be any geometry suitable for providing structural support for tube wall 26, such as a ribbon. Furthermore, member 28 may be a single member 28 lead or a plurality of member 28 leads. Importantly, member 28 should comprise a material which, when helically bonded in tension to the tube wall 26, provides sufficient hoop stress to structurally strengthen tube wall 26. In addition, as can be appreciated from the foregoing discussion, the material of member 28 must be compatible with the material of tube wall 26 to provide for effective bonding. In the present invention, helical structural member 28 is composed of tungsten, but it is to be understood that other materials may be used which fulfill the strength and bonding requirements discussed above, such as molybdenum, stainless steel, or nickel. For the preferred embodiment shown in FIG. 2, member 28 is bonded to tube wall 26 by nickel or other suitable electroplating.

In addition to the material requirements of structural member 28 disclosed above, it will be recognized by the skilled artisan that the dimensions of member 28 must be selected to provide sufficient structural support for tube wall 26, on one hand, while minimizing the cross section of guide wire 18 on the other. In the embodiment shown in FIG. 2, helical structural member 28 is two thousandths (0.002) of an inch thick. Thus, it will be appreciated that the outside diameter 30 of hollow guide wire 18 is the sum of outer tube wall diameter 22, plus twice the thickness of helical structural member 28. This makes the overall outside diameter for device 10 approximately twenty thousandths (0.020) of an inch.

As the skilled artisan will readily appreciate, the angular pitch 32 between successive coils of helical structural member 28, shown in FIG. 2 by dashed lines, should be selected to provide for both balloon 16 steerability, as well as for sufficient torque transmission through guide wire 18 to permit inserting balloon 16 into curved blood vessels. In fact, the present invention envisions a pitch 32 along the length of guide wire 18 which can be varied between twenty (20) and sixty (60) degrees, as steerability and torque transmission requirements dictate. For example, pitch 32 may be relatively high (about forty-five (45) degrees) at the proximal end 34 of guide wire 18 for maximum torque transmission. Pitch 32 may then be gradually or suddenly reduced to thirty (30) degrees at the distal end 36 of guide wire 18, to provide for more flexibility and hence greater steerability of balloon 16.

As shown in detail in FIG. 2, tube 20 is connected in fluid communication with a hollow flexible polymeric tube portion 37. Tube 20 and polymeric tube portion 37 may be attached to each other by any suitable means, such as by epoxy bonding. Polymeric tube portion 37 may be made of any suitable flexible material, such as polyimid, or may be a combination of a polyetherimid layer covered by a polyimid coating. Additionally, a polymeric covering 39 is shown which surrounds and covers both tube 20 and polymeric tube portion 37. As further shown in FIG. 2, composite tube portion 37 is in turn connected in fluid communication with end 38 of balloon 16 by bonding tube portion 37 to end 38 in any suitable manner well known in the art. Thus, a continuous fluid passageway exists through tube 20, polymeric tube portion 37, and into balloon 16. Furthermore, as shown in FIG. 2, end 41 of helical structural member 28 is embedded in tube portion 37 to strengthen portion 37.

With regard to balloon 16, it is to be understood that balloon 16 is a hollow inflatable tube which may be made of any standard balloon material, such as polyethylene terephthalate or polyetherimid. Finally, FIG. 2 shows that a spring member 44 is disposed within balloon 16. Spring member 44 is attached in compression by any suitable manner well known in the art, e.g. electroplating, at its ends 46 and 48 to guide wire 18 and extension 40, respectively. More specifically, end 46 of spring member 44 is embedded within polymeric tube portion 37 and electroplated to end 45 of tube 20.

Figure 3A:
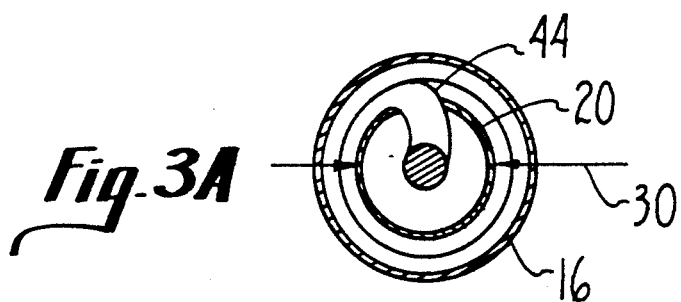
FIG. 3A is a cross-sectional view of an inflated balloon of the angioplasty catheter device of the present invention as seen along the line 3—3 of FIG. 1.
Figure 3B:
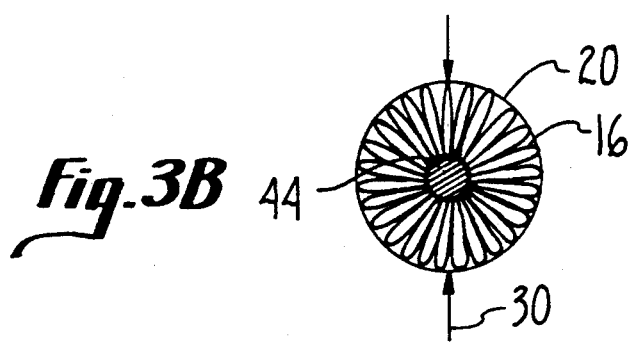
FIG. 3B is a cross-sectional view of the balloon of the angioplasty catheter device as seen along the line 3—3 in FIG. 1, when the balloon is deflated.

The effect of spring member 44 is best seen by cross referencing FIGS. 3A and 3B. FIG. 3A shows balloon 16 in its inflated state, with internal spring member 44 relatively compressed. In contrast, the cross section of the balloon 16 shown in FIG. 3B has a comparatively narrow, pleated geometry when balloon 16 is deflated. Even when balloon 16 is deflated, spring member 44 is still somewhat in a state of compression. It will therefore be appreciated that because spring member 44 is in constant compression, spring member 44 tends to force guide wire 18 and guide wire extension 40 away from each other. This expansion tendency of spring member 44 in turn causes balloon 16, which is attached to both guide wire 18 and extension 40, to fold in pleats around spring 44 when balloon 16 is deflated, as shown in FIG. 3B in any suitable manner well known in the art. Thus, when balloon 16 is deflated, the effect of spring member 44 is to reduce the cross-sectional diameter of balloon 16 to substantially the same diameter as outer diameter 30 of guide wire 18 and guide wire extension 40, thereby facilitating insertion and withdrawal of angioplasty device 10 from blood vessel 14. Moreover, it will be appreciated that when balloon 16 is deflated to its pleat-like shape shown in FIG. 3B, impedance of blood flow through blood vessel 14 by angioplasty device 10 is minimized. On the other hand, spring member 44 does not substantially inhibit expansion of balloon 16 when balloon 16 is infused with fluid.

In addition to the foregoing considerations, spring member 44 is constructed to transfer any torque that is applied at spring end 46 through spring member 44 to spring end 48. In the embodiment shown in FIG. 2, spring member 44 is a stainless steel ribbon-like structure with a width 56 of approximately six thousandths (0.006) of an inch. As intended for the present invention, spring member 44 transfers torque applied to guide wire 18 to extension 40, thereby facilitating the steerability of balloon 16 and substantially preventing windup, or twisting, of balloon 16 when balloon 16 is either inflated or deflated.

As shown in FIG. 2, a hydrophilic porous plug 47 approximately five one thousandths (0.005) of an inch in diameter is positioned substantially coaxially with balloon 16 within end 42 of balloon 16. Plug 47 extends from balloon 16 into guide extension 40. Plug 47 facilitates filling device 10 and balloon 16 with fluid to purge device 10 of air prior to operational use. To this end, plug 47 may be made of any suitable material, such as porous polyethylene or porous teflon. Importantly, the pores of plug 47 are large enough to permit the passage of air through plug 47 and out of extension 40 until substantially all of plug 47 has been wetted. Preferably, the pores of plug 47 have diameters between approximately four millionths of an inch and twenty millionths of an inch. (0.000004–0.00002 inches). When substantially all of plug 47 has been wetted, substantially no fluid (air or liquid) can pass through plug 47.

As previously disclosed, a wire extension 40 is attached to balloon 16 and spring member 44. Extension 40 includes a radiopaque flexible member 60, which is composed of a suitable material, such as gold or tungsten. The pitch 66 between successive coils of radiopaque flexible member 60 may be varied according to the steerability and pushability considerations discussed above. Extension 40 also has a steerable tip 62 integrally attached to a thin tape 64, which provide structural support to extension 40. Further, the steerability of device 10 is provided for by tape 64 which may be bent at an angle suitable for the particular application of angioplasty device 10. As is well known to the skilled artisan, the bendability of tape 64 facilitates guiding device 10 through blood vessel 14. In the embodiment shown in FIG. 2, tape 64 is a one to three thousandths (0.001–0.003) inch wide ribbon, and, like tip 62, is composed of tungsten, although any material which fulfills the structural and chemical compatibility criteria disclosed previously may be used. To fill any voids within the structure of flexible member 60, and to bond member 60 to tape 64, a suitable epoxy bonding material 68 is used.

OPERATION

Referring to FIGS. 1 and 2, in its operation, the angioplasty catheter device 10 is attached to fluid source 12, for infusing fluid into hollow guide wire 18 as more fully disclosed below. It will be appreciated that balloon 16 is initially deflated, as shown in FIG. 3B, in preparation for the insertion procedure described below for angioplasty catheter device 10. Prior to insertion of device 10 into vessel 14, fluid from source 12 is pumped into device 10 to purge air from device 10. As fluid is pumped into device 10 during the purging process, air is forced out of device 10 through the hydrophilic plug 47 disposed in end 42 of balloon 16. Guide wire extension 40 may then be bent as appropriate for the particular application of angioplasty catheter device 10 to provide for effective guiding of balloon 16. Guide wire extension 40 is next inserted into blood vessel 14. Most likely, this is done by using a short guide catheter (not shown) to establish access to the artery and then inserting catheter 10 through the short guide catheter. Balloon 16, in combination with hollow guide wire 18, is then inserted into blood vessel 14, until balloon 16 has been positioned at the desired location within the lumen of blood vessel 14. Importantly, the hoop stress provided by helical structural member 28 enables guide wire 18 to withstand a relatively large amount of bending as it is inserted into blood vessel 14 before guide wire 18 undergoes plastic deformation. Also, the hoop stress provided by helical structural member 28 makes guide wire 18 less prone to collapsing and buckling during the insertion process.

Once balloon 16 has been positioned at the desired location within the lumen of vessel 14, fluid from source 12 is infused through hollow guide wire 18 into balloon 16. This expands balloon 16 to the approximate shape shown in FIG. 2 and further compresses spring member 44. After the lumen of blood vessel 14 has been thereby dilated, fluid within balloon 16 is drained back through hollow guide wire 18 to deflate balloon 16. As fluid is being drained from balloon 16, compressed spring member 44 tends to expand, causing balloon 16 to deflate around spring member 44 in the pleat-like folded shape shown in FIG. 3B. Angioplasty catheter device 10 is then withdrawn from blood vessel 14.

While the particular guide wire with integral angioplasty balloon as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as defined in the appended claims.

I claim:

1. An apparatus for applying pressure to a stenosis in the lumen of a body vessel which comprises;
    a fluid inflatable means;
    a hollow tubular guide wire attached to said inflatable means with an open end of said hollow tubular guide wire in fluid communication with said inflatable means;
    a guide extension fixedly attached to said inflatable means interconnecting said guide extension and said guide wire;
    a helical structural member bonded to said wire for strengthening said wire, said helical member defining a plurality of coils; and
    an elongated flexible structural member disposed inside said fluid inflatable means and fixedly attached to said guide extension and said guide wire.

2. An apparatus as recited in claim 1 wherein said fluid inflatable means is a balloon.

3. An apparatus as recited in claim 1 wherein said tubular guide wire is stainless steel, gold, or platinum.

4. An apparatus as recited in claim 1 wherein said helical structural member is a wire made of tungsten, molybdenum, or high-strength stainless steel.

5. An apparatus as recited in claim 1 wherein said helical structural member is a ribbon made of tungsten, molybdenum, or high-strength stainless steel ribbon.

6. An apparatus as recited in claim 4 or 5 wherein said helical structural member is formed with a pitch between successive said coils in the range of twenty to sixty degrees.

7. An apparatus as recited in claim 6 wherein said helical angle is variable along the length of said guide wire.

8. An apparatus as recited in claim 1 wherein said structural member comprises a spring mounted in compression between said guide wire and said guide extension to urge said guide extension and said guide wire apart, to collapse said fluid inflatable means to reduce the radial cross-sectional areas of said fluid inflatable means.

9. An apparatus for applying pressure to a stenosis in the lumen of a body vessel which comprises:
    a balloon;
    a hollow tubular guide wire attached in fluid communication with said balloon;
    a guide extension fixedly attached to said balloon with said balloon interconnecting said guide extension and said guide wire;
    a helical structural member bonded to said wire by nickel electroplating for strengthening said wire, said helical member defining a plurality of coils; and
    an elongated flexible structural member disposed inside said fluid inflatable means and fixedly attached to said guide extension and said guide wire.

10. An apparatus for applying a pressure to a stenosis in the lumen of a body vessel which comprises:
    a balloon;
    a hollow tubular guide wire attached in fluid communication with said balloon;
    a guide extension fixedly attached to said balloon with said balloon interconnecting said guide extension and said guide wire;
    a helical structural member bonded to said wire for strengthening said wire, said helical member disposed inside said fluid inflatable means and fixedly attached to said guide extension and said guide wire; and
    a hydrophilic plug positioned within said balloon near said guide extension to permit the passage of gas through said plug and said guide extension when said plug is not substantially wet and to substantially prevent the passage of gas through said plug and said guide extension when said plug is substantially wet.

11. An apparatus for applying pressure to a stenosis in the lumen of a body vessel which comprises:
    a balloon;
    a hollow tubular guide wire attached in fluid communication with said balloon;
    a guide extension fixedly attached to said balloon with said balloon interconnecting said guide extension and said guide wire;
    a helical structural member bonded to said wire for strengthening said wire, said helical member defining a plurality of coils;
    an elongated flexible structural member disposed inside said fluid inflatable means and fixedly attached to said guide extension and said guide wire; and
    a flexible hollow polymeric portion for interconnecting said balloon and said guide wire, said hollow polymeric portion having a first end and a second end, said first end being bonded in fluid communication to said guide wire, said second end being bonded in fluid communication to said balloon.

12. An apparatus for dilating a body vessel which comprises:
    a hollow inflatable tube;
    positioning means fixedly attached in fluid communication with said inflatable tube to position said inflatable tube within said body vessel;
    structural means helically bonded to said positioning means to strengthen and support said positioning means;
    a guide extension bonded to said inflatable tube for steering said apparatus;
    an elongated spring member positioned inside said inflatable tube and bonded to said positioning means and said guide extension for urging said guide extension away from said positioning means to collapse said inflatable tube; and
    a hydrophilic plug positioned within said balloon near said guide extension to permit the passage of gas through said plug and said guide extension when said plug is not substantially wet and to substantially prevent the passage of gas through said plug and said guide extension when said plug is substantially wet.

13. An apparatus for dilating a body vessel as recited in claim 12 wherein said inflatable tube is a balloon.

14. An apparatus for dilating a body vessel as recited in claim 13 wherein said positioning means is a hollow tubular guide wire made of stainless steel, gold, or platinum.

15. An apparatus for dilating a body vessel as recited in claim 14 further comprising a flexible hollow polymeric portion for interconnecting said balloon and said guide wire, said hollow polymeric portion having a first end and a second end, said first end being bonded in fluid communication to said guide wire, said second end being bonded in fluid communication to said balloon.

16. An apparatus for dilating a body vessel as recited in claim 14 wherein said structural means is a helical member.

17. An apparatus for dilating a body vessel as recited in claim 16 wherein said helical member is bonded to said guide wire by nickel electroplating.

18. An apparatus for dilating a body vessel as recited in claim 16 wherein said helical member is a wire made of tungsten, molybdenum, or high-strength stainless steel.

19. An apparatus for dilating a body vessel as recited in claim 18 wherein said helical member is a ribbon made of tungsten, molybdenum, or high-strength stainless steel.

20. An apparatus for dilating a body vessel as recited in claim 18 or 19 wherein said helical member is formed with a pitch between successive coils in the range of twenty to sixty degrees.

21. An apparatus for dilating a body vessel as recited in claim 20 wherein said helical angle is variable along the length of said guide wire.

22. An apparatus for dilating a body vessel as recited in claim 12 wherein said spring member is mounted in compression between said positioning means and said guide extension.

23. An angioplasty device for urging against a stenosis in a blood vessel, which comprises:
   an expandable balloon having a first end and a second end, said balloon having an expanded configuration wherein said balloon is radially enlarged to urge against said stenosis and a collapsed configuration wherein said balloon is radially reduced relative to said expanded configuration to facilitate moving said balloon within said blood vessel;
   an elongated hollow tube bonded to said first end of said balloon, said tube having an open end placed through said first end of said balloon and being in fluid communication with said balloon for selectively establishing said expanded and said collapsed configurations;
   a flexible guide extension bonded to said second end of said balloon for guiding said balloon within said blood vessel; and
   an elongated flexible spring positioned inside said balloon and bonded to said tube and said guide extension to urge said tube away form said guide extension to urge said balloon into said collapsed configuration.

24. An angioplasty device as recited in claim 23 further comprising a helical member bonded to said tube to strengthen said tube.

* * * * *